US00PP37652P2

(12) United States Plant Patent
van Dijk

(10) Patent No.: US PP37,652 P2
(45) Date of Patent: Aug. 25, 2026

(54) ***ANTHURIUM* PLANT NAMED 'AN2860280'**

(50) Latin Name: *Anthurium andreanum*
Varietal Denomination: 'AN2860280'

(71) Applicant: ANTHURA B.V., Bleiswijk (NL)

(72) Inventor: Jan van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/323,756

(22) Filed: Sep. 9, 2025

(51) Int. Cl.
*A01H 5/02* (2018.01)
*A01H 6/10* (2018.01)

(52) U.S. Cl.
USPC ..... Plt./365

(58) Field of Classification Search
USPC ..... Plt./365, 369
See application file for complete search history.

(56) References Cited

U.S. PATENT DOCUMENTS

PP33,912 P2 * 1/2022 Van Dijk ..... A01H 6/00
Plt./384

* cited by examiner

*Primary Examiner* — Susan Mccormick Ewoldt
*Assistant Examiner* — Zachariah Allan Kay
(74) *Attorney, Agent, or Firm* — C. Anne Whealy

(57) ABSTRACT

A new and distinct cultivar of *Anthurium* plant named 'AN2860280', characterized by its compact, upright to outwardly arching plant habit; freely clumping growth habit; bushy and dense plants; narrowly cordate dark green-colored leaves; freely flowering habit; inflorescences that are positioned above the foliar plane on upright scapes; cordate-shaped spathes that are red in color; and white and yellow-colored spadices.

2 Drawing Sheets

Figure 1:
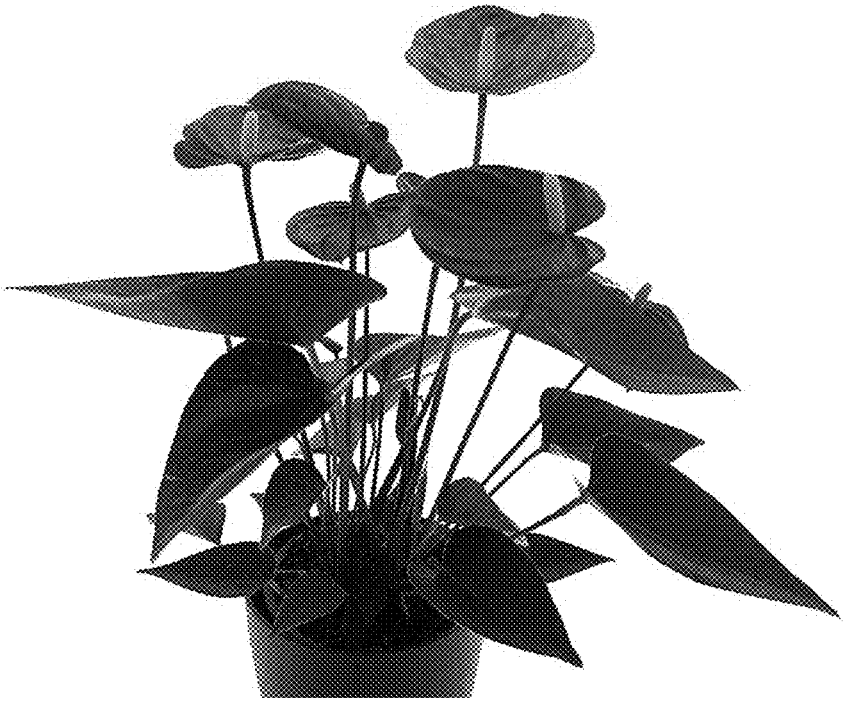

Botanical designation: *Anthurium andreanum.*
Cultivar denomination: 'AN2860280'.

CROSS-REFERENCED TO CLOSELY-RELATED APPLICATION

A European Community Plant Breeder's Rights application for the instant plant was filed by the Applicant/Assignee of the instant application, Anthura B.V. of Bleiswijk, The Netherlands on Nov. 20, 2024, application number 2024/2685. Foreign priority is not claimed to this application.

BACKGROUND OF THE INVENTION

The present invention relates to a new and distinct cultivar of *Anthurium* plant, botanically known as *Anthurium andreanum,* commonly referred to as Flamingo Flower and hereinafter referred to by the name 'AN2860280'.

The new *Anthurium* plant is a product of a controlled breeding program conducted by the Inventor in Bleiswijk, The Netherlands. The objective of the breeding program is to create new *Anthurium* plants with durable red-colored spathes.

The new *Anthurium* plant originated from a cross-pollination made by the Inventor in October 2015 in Bleiswijk, The Netherlands of a proprietary breeding selection of *Anthurium andreanum* identified as code number 11-027565-0001, not patented, as the female, or seed, parent with a proprietary breeding selection of *Anthurium andreanum* identified as code number 11-025991-0002, not patented, as the male, or pollen, parent. The new *Anthurium* was discovered and selected by the Inventor as a single flowering plant within the progeny of the stated cross-pollination in a controlled greenhouse environment in Bleiswijk, The Netherlands in October 2017.

Asexual reproduction of the new *Anthurium* plant by in vitro meristem propagation in a controlled environment in Bleiswijk, The Netherlands since October 2017 has shown that the unique features of this new *Anthurium* are stable and reproduced true to type in successive generations of asexual reproduction.

SUMMARY OF THE INVENTION

Plants of the new *Anthurium* have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'AN2860280'. These characteristics in combination distinguish 'AN2860280' as a new and distinct *Anthurium* plant:

1. Compact, upright to outwardly arching plant habit.
2. Freely clumping growth habit; bushy and dense plants.
3. Narrowly cordate dark green-colored leaves.
4. Freely flowering habit.
5. Open inflorescences that are positioned above the foliar plane on upright scapes.
6. Cordate-shaped spathes that are red in color.
7. White and yellow-colored spadices.

Plants of the new *Anthurium* differ primarily from plants of the female parent selection in the following characteristics:

1. Leaves of plants of the new *Anthurium* are narrower than leaves of plants of the female parent selection.

2. Spadices of plants of the new *Anthurium* are shorter than spadices of plants of the female parent selection.

Plants of the new *Anthurium* differ primarily from plants of the male parent selection in the following characteristics:

1. Spathes of plants of the new *Anthurium* are cordate in shape whereas spathes of plants of the male parent selection are broadly ovate in shape.
2. Spathe apices of plants of the new *Anthurium* are abruptly acute with mucronate apex whereas spathe apices of plants of the male parent selection are moderately acuminate.

Plants of the new *Anthurium* can also be compared to plants of *Anthurium andreanum* 'ANTHGRICJE', disclosed in U.S. Plant Pat. No. 33,912. In side-by-side comparisons, plants of the new *Anthurium* differ primarily from plants of 'ANTHGRICJE' in the following characteristics:

1. Leaves of plants of the new *Anthurium* are narrowly cordate whereas leaves of plants of 'ANTHGRICJE' are ovate.
2. Spathes of plants of the new *Anthurium* are not as glossy as spathes of plants of 'ANTHGRICJE'.
3. Spadices of plants of the new *Anthurium* are shorter than spadices of plants of 'ANTHGRICJE'.

BRIEF DESCRIPTION OF THE PHOTOGRAPHS

The accompanying photographs illustrate the overall appearance of the new *Anthurium*. The photographs show the colors as true as it is reasonably possible to obtain in colored reproductions of this type. Colors in the photographs may differ slightly from the color values cited in the detailed botanical description which accurately describe the colors of the new *Anthurium*.

The photograph on the first sheet (FIG. 1) is a side perspective view of a typical plant of 'AN2860280' grown in a container.

Figure 2:
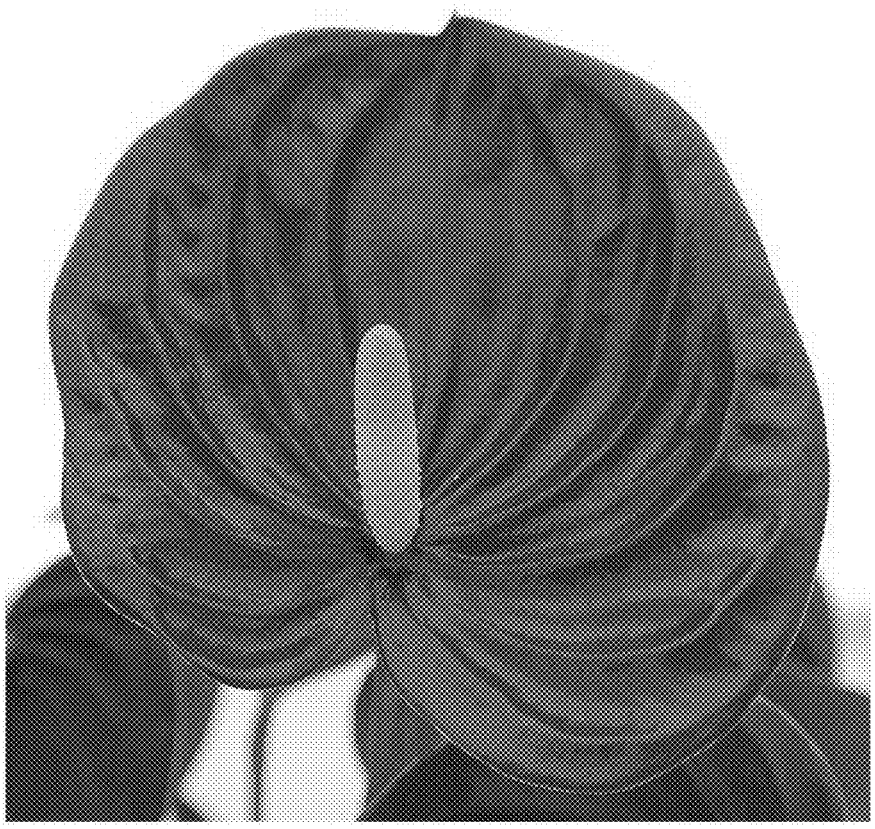

The photograph on the second sheet (FIG. 2) is a close-up view of a typical inflorescence of 'AN2860280'.

DETAILED BOTANICAL DESCRIPTION

The aforementioned photographs and following observations and measurements describe plants grown in 12-cm containers during the winter and early spring in a glass-covered greenhouse in Bleiswijk, The Netherlands. Plants were grown under conditions and practices which approximate those generally used in commercial *Anthurium* production. During the production of the plants, day and night temperatures ranged from about 19° C. to about 22.5° C. and light levels ranged from about 100 μmol to about 200 μmol. Plants were ten months from planting young rooted plants when the photographs and the detailed description were taken. In the following description, color references are made to The Royal Horticultural Society Colour Chart, 2015 Edition, except where general terms of ordinary dictionary significance are used.

Botanical classification: *Anthurium andreanum* 'AN2860280'.

Parentage:

*Female, or seed, parent*.—Proprietary breeding selection of *Anthurium andreanum* identified as code number 11-027565-0001, not patented.

*Male, or pollen, parent*.—Proprietary breeding selection of *Anthurium andreanum* identified as code number 11-025991-0002, not patented.

Propagation:

*Type*.—By in vitro meristem propagation.

*Time to initiate roots, summer and winter*.—About two weeks at temperatures ranging from about 19° C. to about 22.5° C.

*Time to produce a rooted young plant, summer and winter*.—About six to eight weeks at temperatures ranging from about 19° C. to about 22.5° C.

*Root description*.—Medium in thickness, fibrous; typically creamy white slightly tinged with pink in color; actual color of the roots is dependent on substrate composition, water quality, fertilizer type and formulation, substrate temperature and physiological age of roots.

*Rooting habit*.—Freely branching, medium density.

Plant description:

*Plant shape*.—Compact, upright to outwardly spreading plant habit; overall shape, broadly elliptic to roughly globular.

*Growth habit*.—Freely clumping habit imparting a bushy and dense appearance; in a single year of production, about 40 individual plants can be harvested per plant; and moderately vigorous growth habit.

*Plant height, from soil level to top of leaf plane*.—About 22.9 cm.

*Plant height, from soil level to top of inflorescences*.—About 30.8 cm.

*Plant diameter or spread*.—About 41.6 cm.

Leaf description:

*Arrangement*.—Alternate; simple.

*Length*.—About 13.9 cm.

*Width*.—About 8.4 cm.

*Shape*.—Narrowly cordate.

*Apex*.—Bluntly acute with a mucronate tip.

*Base*.—Cordate.

*Margin*.—Entire; coarsely undulate.

*Texture, upper and lower surfaces*.—Smooth, glabrous; moderately coriaceous.

*Venation pattern*.—Pinnate.

*Color*.—Developing leaves, upper surface: Close to a blend of 152A and N199C; narrow marginal edges, close to 187C; mucronate apices, close to 53B; areas adjacent to venation, close to 144A. Developing leaves, lower surface: Close to 199A; narrow marginal edges, close to 187C; mucronate apices, close to 53B; towards the base, close to 144C; venation, close to N199B. Fully expanded leaves, upper surface: Close to NN137A; narrow marginal edges, close to 144A; mucronate apices, close to 146A; venation, close to 144A. Fully expanded leaves, lower surface: Close to 146B; venation, close to 151A.

*Petioles*.—Length: About 14 cm. Diameter: Distally, about 3 mm and proximally, about 5 mm. Texture, upper and lower surfaces: Smooth, glabrous. Color, upper and lower surfaces: Close to 146C. Geniculum length: About 1.6 cm. Geniculum diameter: About 3.5 mm. Geniculum texture, upper and lower surfaces: Smooth, glabrous. Geniculum color, upper surface: Close to 146B. Geniculum color, lower surface: Close to 144B. Wing length: About 1.6 cm. Wing diameter: About 3.5 mm. Wing texture: Smooth, glabrous. Wing color: Close to 143B; towards the margins, close to 144C.

Inflorescence description:

*Inflorescence arrangement and flowering habit.*—Spathes with spadices; open inflorescences held above the foliar plane on strong scapes; flowering structures arise from leaf axils; freely and continuous flowering year-round in controlled temperature greenhouses in The Netherlands; typically about six developing and developed inflorescences per plant at one time; inflorescence development commences about 2.5 to 3.5 months after planting rooted young plants.

*Inflorescence longevity.*—On the plant, depending on temperature, spathes maintain good substance for about two months; inflorescences persistent.

*Fragrance.*—None detected.

*Spathes.*—Length: About 9.1 cm. Width: About 9.1 cm. Shape: Cordate; slightly to moderately concave. Apex: Abruptly acute with mucronate apex. Base: Cordate. Margin: Entire; occasionally slightly revolute. Aspect: About 80° to 100° from the scape axis. Texture, upper and lower surfaces: Smooth, glabrous; moderately coriaceous. Color: When developing, front surface: Close to 46B; mucronate apices, close to 160A. When developing, rear surface: Close to 45B; narrow marginal edges, close to N45A; mucronate apices, close to 160A. Fully developed, front surface: Close to N45A; narrow marginal edges, close to 53A; mucronate apices, close to 162B. Fully developed, rear surface: Close to 45B; towards the base, close to 47D; narrow marginal edges, close to N45B; mucronate apices, close to 160A.

*Spadices.*—Length: About 2.6 cm. Diameter: About 6.5 mm. Shape: Cylindrical, slightly tapering towards the apex; apex, obtuse; base, obtuse; in cross-section, rounded. Aspect: About 0° to 30° from the scape axis. Color, immature: Close to 15B; distally, close to N144D. Color, mature: Close to 158B; distally, close to NN155A. Flowers: Type: Hermaphroditic. Quantity per spadix: About 110. Height: About 1 mm. Diameter: About 2 mm. Shape: Roughly square. Anther color: Close to 158B. Pollen amount: Scarce. Pollen color: Close to 155B. Stigma color: Close to 199A. Ovary color: Close to 151C.

*Scapes.*—Length: About 22.5 cm. Diameter: About 3 mm. Aspect: About 20° from vertical. Color: Close to 144A and 175A.

*Seed and fruit.*—To date, seed and fruit development has not been observed on plants of the new *Anthurium.*

Pathogen & pest resistance: To date, plants of the new *Anthurium* have not been observed to be resistant to pathogens or pests common to *Anthurium* plants.

Temperature tolerance: Plants of the new *Anthurium* have been observed to be tolerant to high temperatures of about 30° C. and to be hardy to USDA Hardiness Zone 10.

It is claimed:

1. A new and distinct *Anthurium* plant named 'AN2860280' as herein illustrated and described.

* * * * *